United States Patent
Freudenthal et al.

(10) Patent No.: US 10,950,253 B2
(45) Date of Patent: Mar. 16, 2021

(54) VOCAL FEEDBACK DEVICE AND METHOD OF USE

(71) Applicant: Board of Regents, The University of Texas System, Austin, TX (US)

(72) Inventors: Eric A. Freudenthal, El Paso, TX (US); Lluvia Mendiola, El Paso, TX (US); Vannesa Mueller, El Paso, TX (US); Celete Orozco, El Paso, TX (US); Kendra Rosales, El Paso, TX (US)

(73) Assignee: Board of Regents, The University of Texas System, Austin, TX (US)

(*) Notice: Subject to any disclaimer, the term of this patent is extended or adjusted under 35 U.S.C. 154(b) by 111 days.

(21) Appl. No.: 16/271,372

(22) Filed: Feb. 8, 2019

(65) Prior Publication Data

US 2019/0251982 A1    Aug. 15, 2019

Related U.S. Application Data

(60) Provisional application No. 62/628,907, filed on Feb. 9, 2018, provisional application No. 62/628,903, filed on Feb. 9, 2018.

(51) Int. Cl.
| | |
|---|---|
| *G10L 21/00* | (2013.01) |
| *G10L 25/00* | (2013.01) |
| *G10L 21/013* | (2013.01) |
| *H04R 1/40* | (2006.01) |
| *G10L 25/90* | (2013.01) |

(Continued)

(52) U.S. Cl.
CPC .......... *G10L 21/013* (2013.01); *A61B 5/4803* (2013.01); *A61B 5/486* (2013.01); *G10L 25/90* (2013.01); *H04R 1/406* (2013.01); *H04R 3/005* (2013.01); *A61B 2562/0204* (2013.01); *G10L 2021/0135* (2013.01)

(58) Field of Classification Search
None
See application file for complete search history.

(56) References Cited

U.S. PATENT DOCUMENTS

| | | | |
|---|---|---|---|
| 6,410,568 B1 | 6/2002 | Schastak et al. | |
| 8,208,664 B2 * | 6/2012 | Iwasaki | H04M 3/568 |
| | | | 381/310 |

(Continued)

OTHER PUBLICATIONS

Freudenthal et al., "Self-Adjusting Fundamental Frequency Accentuation Subsystem for Natural Ear Device," U.S. Appl. No. 16/271,237, filed Feb. 8, 2019, 41 pages.

(Continued)

*Primary Examiner* — Satwant K Singh
(74) *Attorney, Agent, or Firm* — Yee & Associates, P.C.

(57) ABSTRACT

A vocal feedback device comprising: a microphone; a fundamental frequency accentuator electrically connected to the microphone, a delay circuit electrically connected to the fundamental frequency accentuator, and a speaker electrically connected to the delay circuit. The device configured to convert vocal utterances received at the microphone into an electrical signal, impose a time delay before transmitting the electrical signal, after the time delay, transmit the electrical signal to the speaker, and convert the electrical signal to an audio signal using the speaker, the audio signal being a replication of the vocal utterances.

20 Claims, 3 Drawing Sheets

(51) Int. Cl.
*A61B 5/00* (2006.01)
*H04R 3/00* (2006.01)

(56) References Cited

U.S. PATENT DOCUMENTS

| | | | |
|---|---|---|---|
| 8,566,092 B2 | 10/2013 | Liu et al. | |
| 9,240,193 B2 * | 1/2016 | James | G10L 21/00 |
| 9,286,863 B2 * | 3/2016 | Moon | H04S 7/305 |
| 9,589,574 B1 * | 3/2017 | Klimanis | G10L 25/90 |
| 9,654,861 B1 * | 5/2017 | Klimanis | G10L 25/18 |
| 9,773,426 B2 * | 9/2017 | Freudenthal | G10H 1/44 |
| 10,045,115 B2 * | 8/2018 | Klimanis | G10L 25/84 |
| 10,531,178 B2 * | 1/2020 | Klimanis | H04R 29/004 |
| 10,595,117 B2 * | 3/2020 | Klimanis | G10L 21/0232 |
| 2004/0194610 A1 * | 10/2004 | Davis | H04R 5/04 |
| | | | 84/466 |
| 2006/0178876 A1 * | 8/2006 | Sato | H03G 3/34 |
| | | | 704/225 |
| 2010/0036660 A1 | 2/2010 | Bennett | |
| 2011/0142258 A1 | 6/2011 | Beer | |
| 2013/0182862 A1 | 7/2013 | Disch | |
| 2014/0207443 A1 | 7/2014 | Hosoya et al. | |
| 2015/0350779 A1 | 12/2015 | McNutt et al. | |
| 2017/0076738 A1 * | 3/2017 | Freudenthal | G10L 21/0388 |
| 2018/0061431 A1 | 3/2018 | Hönig | |
| 2019/0251981 A1 * | 8/2019 | Freudenthal | G10L 21/013 |

OTHER PUBLICATIONS

Office Action, dated Dec. 10, 2020, regarding USPTO U.S. Appl. No. 16/271,237, 11 pages.

\* cited by examiner

VOCAL FEEDBACK DEVICE AND METHOD OF USE

CROSS-REFERENCE TO RELATED APPLICATION(S)

This application claims the benefit of U.S. Provisional Patent Application No. 62/628,907 filed on Feb. 9, 2018, and Provisional Patent Application No. 62/628,903 filed on Feb. 9, 2018, the contents of each are incorporated herein by reference.

BACKGROUND INFORMATION

1. Field

The present disclosure relates to vocal feedback devices and particular to methods and devices for helping a user improve vocalizations or for training a user's voice.

2. Background

A variety of people suffer from vocal-related conditions that can reduce their ability to speak in a preferred manner. For example, a user may suffer from Parkinson's disease and have reduced volume and monotonic quality. Currently, there is no known device that can improve vocal quality with a desired degree of intrusiveness.

SUMMARY

An example vocal feedback device to train a user's voice for improved tonal qualities of speech including a microphone directed at the user, a fundamental frequency accentuator coupled to the microphone, a delay circuit coupled to the fundamental frequency accentuator, where the delay circuit is configured to impose a time delay before transmitting an electrical signal received from the fundamental frequency accentuator, and a speaker coupled to the delay circuit, where the speaker is configured to convert the electrical signal to an audio signal directed at the user.

An example vocal feedback device to assist the speech of a user including a device in receipt of input sound waves generated from the speech of the user, an electrical signal produced from the input sound waves and generated by the device, a modified electrical signal generated by the device where a fundamental frequency of the input sound waves is accentuated in the modified electrical signal, and a time delay introduced to the modified electrical signal before the modified electrical signal is converted to output sound waves by the device.

An example method for improving a vocalization of a user including positioning a vocal feedback device, generating an electrical signal from the vocalization, generating a modified electrical signal from the electrical signal, imposing a delay on the modified electrical signal, and transmitting sound waves generated from the modified electrical signal.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account that current vocal training techniques do not provide results as great as desired in terms of improving a user's voice to behave as the user desires. Thus, the illustrative embodiments provide a vocal feedback device for a self-feedback mechanism so that a user can train the user's own voice to achieve a desired result or enable improved speech of the user when in range of the device.

People often are unaware of the tonal qualities of their speech. What a person sounds like to themselves while they are speaking is often very different from what the person sounds like to others. This difference can be heard by a user when a user listens to a recording of their speech, for example in a phone message, a podcast, a video recording, etc. Often people are surprised by how different they sound when compared to how they sound to themselves while speaking. People desire their vocal communications to be effective. A variety of people suffer from vocal-related conditions which can reduce their ability to speak in a preferred manner. For example, a user may have been born with common otolaryngologic issues or, more seriously, suffer from diseases such as Parkinson's that affect volume and monotonic quality of their speech. Contributing to the problem, the acoustic signal from human utterances is dominated by distracting harmonics. Distracting harmonics make it difficult for a user to detect the fundamental frequency of a user's utterance. This condition is colloquially referred to as "tin ear."

Identification and realization of the fundamental frequency of a user's utterance would contribute to the ability for a user to communicate effectively. Fundamental frequencies contain the lyrical prosody of speech that are primarily frequency and amplitude, which, in the English language, substantially convey emotion.

An exemplary vocal feedback device disclosed herein increases the user's awareness of the tonal qualities, cadence, and amplitude of their utterances by detecting and accentuating the fundamental frequency of their utterance and providing a feedback delay of their utterances to them containing the accentuated fundamental frequency. This awareness can increase the user's ability to effectively and persistently modulate these aspects of their voice. An exemplary vocal feedback device disclosed herein may also increase the ability to accurately convey emotion in spoken presentation.

The self-feedback features of an exemplary vocal feedback device are relevant to the following (and other) therapies: Voice training for transgender persons, speech therapy for people on the autism spectrum, speech therapy for persons with conditions such as Parkinson's disease, fluency disorders such as stuttering or cluttering, or vocal nodules, as well as for ordinary people who desire a more pragmatic awareness of their own speech.

In all of these therapeutic applications, an exemplary vocal feedback device can potentially be used both during therapy sessions and in unsupervised contexts to enable the user to modify functional and/or pragmatic aspects of their utterances. An exemplary vocal feedback device can potentially be used unbeknownst to the user and/or others around the user.

Certain terms are used throughout the following description and claims to refer to particular system components and configurations. As one skilled in the art will appreciate, the same component may be referred to by different names. This document does not intend to distinguish between components that differ in name but not function.

The term "couple" or "couples" is intended to mean either an indirect or direct connection. Thus, if a first device couples to a second device, that connection can be through a direct connection, or through an indirect connection via other devices and connections. An electronically coupled connection may be wired or wireless.

When an input/output signal or an utterance "corresponds" to a fundamental frequency or spectrum of frequencies, it is intended to mean that the sound heard by a user resulting from the input/output signals or utterances is the vocal sound containing the fundamental frequency or spectrum of frequencies. Thus, if an output signal corresponds to a particular fundamental frequency, the sound heard as a result of the output signal is the vocal sound from the user making an utterance at the particular fundamental frequency.

The foregoing description of the figures is provided for the convenience of the reader. It should be understood, however, that the embodiments are not limited to the precise arrangements and configurations shown in the figures. Also, the figures are not necessarily drawn to scale, and certain features may be shown exaggerated in scale or in generalized or schematic form, in the interest of clarity and conciseness. The same or similar parts may be marked with the same or similar reference numerals.

While various embodiments are described herein, it should be appreciated that the present invention encompasses many inventive concepts that can be embodied in a wide variety of contexts. The following detailed description of exemplary embodiments, read in conjunction with the accompanying drawings, is merely illustrative and is not to be taken as limiting the scope of the invention, as it would be impossible or impractical to include all of the possible embodiments and contexts of the invention in this disclosure. Upon reading this disclosure, many alternative embodiments of the present invention will be apparent to persons of ordinary skill in the art. The scope of the invention is defined by the appended claims and equivalents thereof.

Illustrative embodiments of the invention are described below. In the interest of clarity, not all features of an actual implementation are described in this specification. In the development of any such actual embodiment, numerous implementation-specific decisions may need to be made to achieve the design-specific goals, which can vary from one implementation to another. It will be appreciated that such a development effort, while possibly complex and time-consuming, would nevertheless be a routine undertaking for persons of ordinary skill in the art having the benefit of this disclosure.

In accordance with various embodiments of this invention, the vocal feedback device assists a person to have greater awareness of various aspects of their voice related to how they pronounce vowels, diction, harmonization with others, and phrasing. To the extent that speech includes modulating similar aspects of voice (pitch, volume, emphasis/attack, vowel sounds, etc), the device can increase users' awareness and intuitively improve their ability to accurately convey emotion in spoken presentation.

Figure 1:
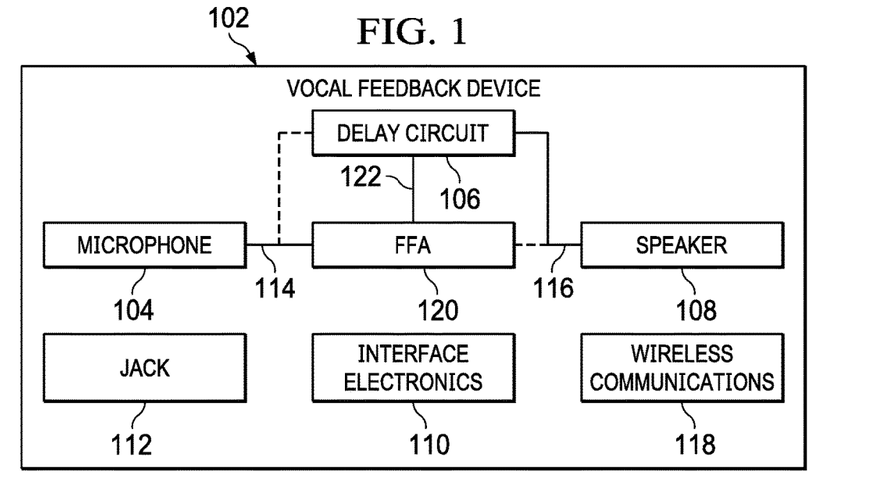
FIG. 1 illustrates a block diagram of a vocal feedback device, in accordance with an illustrative embodiment.

FIG. 1 depicts a block diagram of a vocal feedback device, in accordance with an illustrative embodiment. Vocal feedback device 102 may include microphone 104 for receiving sound waves from the utterances of a user. Microphone 104 may be a directional microphone. A directional microphone is more sensitive to picking up sound from a specific direction while at the same time may block out distracting noise from other directions. Microphone 104 converts the received sound waves into input signal 114. Input signal 114 is electrical signals produced by microphone 104 from the sound waves uttered by a user. Vocal feedback device 102 may include fundamental frequency accentuator (FFA) subsystem 120 coupled to and in electrical communication with microphone 104. Microphone 104 transmits input signal 114 to FFA subsystem 120.

FFA subsystem 120 creates a modified input signal 122 where the fundamental frequency of input signal 114 is accentuated. Modified input signal 122 is electrical signals produced by FFA subsystem 120 from input signal 114. When FFA subsystem 120 accentuates the fundamental frequency of input signal 114, the fundamental frequency and any other remaining frequencies (that have not been filtered out or have not been synthesized) in the utterance are amplified such that the ratio of the effective amplitude of the accentuated fundamental frequency to the other frequencies in modified signal 122 is higher than the ratio of the effective amplitude of the fundamental frequency to the other frequencies in input signal 114 before the accentuating occurs. FFA subsystem 120 attenuates distracting harmonics from the frequency spectrum of input signal 114 so that the distracting harmonics do not contribute significantly to modified input signal 122 transmitted by FFA subsystem 120 to speaker 108.

Vocal feedback device 102 may include delay circuit 106 coupled to and in electrical communication with FFA subsystem 120. FFA subsystem 120 transmits modified input signal 122 to delay circuit 106. Delay circuit 106 introduces a time delay to the electrical signals of input signal 122. In some illustrative embodiments, delay circuit 106 may be a delay and equalization circuit. The equalization may be static or dynamic in order to accentuate aspects of human utterances most relevant for improving the spoken communication from the particular user.

Vocal feedback device 102 may include speaker 108 coupled to and in electrical communication with delay circuit 106. Delay circuit 106 transmits the modified and delayed electrical signals as output signal 116 to speaker 108. Speaker 108 may be a directional speaker. Directional speakers transmit sound in a focused column with less energy dissipation that traditional speakers. Speaker 108 converts output signal 116 into sound waves directed back at the user.

Optionally, delay circuit 106 may be coupled to and in electrical communication with microphone 104 such that delay circuit 106 receives input signal 114 from microphone 104 and introduces the time delay to input signal 114 before FFA subsystem 120 accentuates the fundamental frequency of input signal 114. Accordingly, in this exemplary embodiment, delay circuit 106 transmits modified input signal 122 to FFA subsystem 120 so FFA subsystem can proceed with accentuating the fundamental frequency of modified input signal 122. In this exemplary embodiment, FFA subsystem 120 transmits the modified and delayed electrical signals as output signal 116 to speaker 108.

Vocal feedback device 102 may include interface electronics 110. Interface electronics 110 may be used to change the sensitivity of microphone 104, alter the volume of output of speaker 108, modify the delay duration produced by delay circuit 106, tune a filter or synthesizer of FFA subsystem 120. Interface electronics 110 may be used to affect other aspects of operation of vocal feedback device 102 including but not limited to turning the unit on or off and waveform displays to the user.

Vocal feedback device 102 may be provided with one or more jacks, such as jack 112, in order to support external microphones or external speakers, such as but not limited to remote speakers, earbuds, or a headset. Jack 112 may also be a USB (universal serial bus) outlet so that vocal feedback device 102 may be connected to a computer for further processing and data analysis of the vocal utterance of the user.

Vocal feedback device 102 may be provided with wireless communications 118, such as but not limited to BLUETOOTH®, so that a user may use a wireless microphone, a wireless speaker, wireless earbuds, a wireless headset, wireless connection to a computer for downloading operational data and statistical analysis, or combinations thereof.

The end result is that, in practice, the user more clearly hears their verbal output because vocal feedback device 102 generates a delayed output signal based on an attenuated frequency spectrum of the user's speech that includes an accentuated fundamental frequency.

Figure 2:
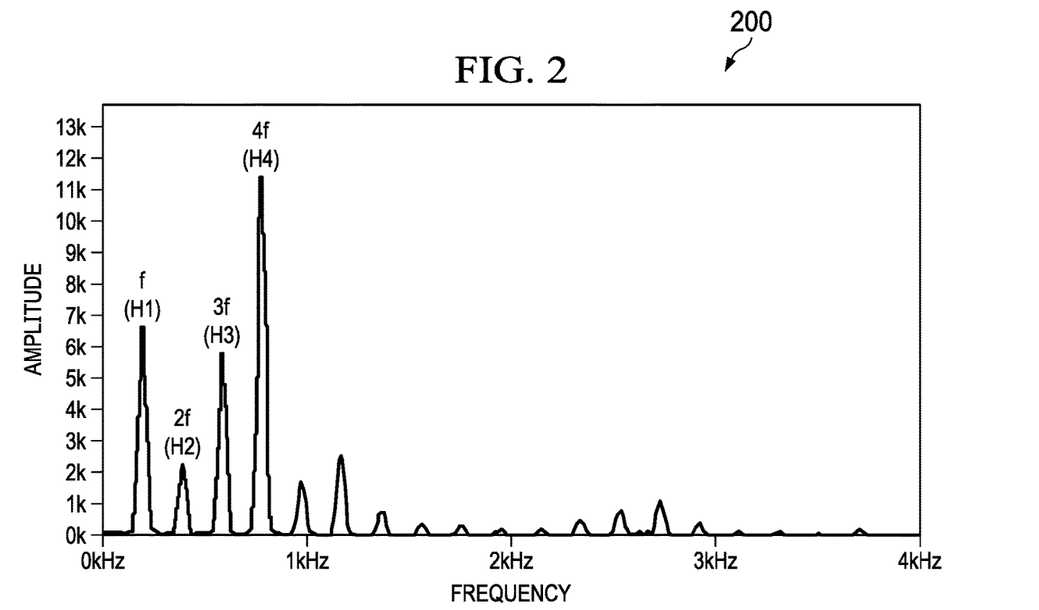
FIG. 2 illustrates a graph of the frequency spectrum of a user's utterance, in accordance with an illustrative embodiment.

FIG. 2 is a graph of an exemplary frequency spectrum of a user's voice, in accordance with an illustrative embodiment. The user's voice may be that described with respect to FIG. 1.

Frequency spectrum graph 200 shows a user's utterances contain a fundamental frequency component f, second harmonic 2f, third harmonic 3f, fourth harmonic 4f, and so on until the amplitude of the harmonics become very small. In this illustration, after the sixth harmonic, the amplitude approaches close to zero. A user's utterances have harmonious and unharmonious frequency components.

The fundamental frequency f and some harmonics including 2f and 4f are harmonious. Odd harmonics such as 3f, 5f, 7f and so on are particularly unharmonious. As explained above, users who have a "tin ear" cannot clearly discern the fundamental frequency of their own utterances due to the associated and coincidental harmonics. A user may improperly identify one or more odd harmonics as the fundamental frequency of their utterance and/or are unable to discern the fundamental frequency that they are uttering. Thus, referring to FIG. 2, a user might identify the loud odd harmonic 3f as their fundamental frequency and believe that this unharmonious odd harmonic is their fundamental frequency, which is undesirable and would contribute to ineffective or misleading (albeit unintentional) communication traits.

Figure 3:
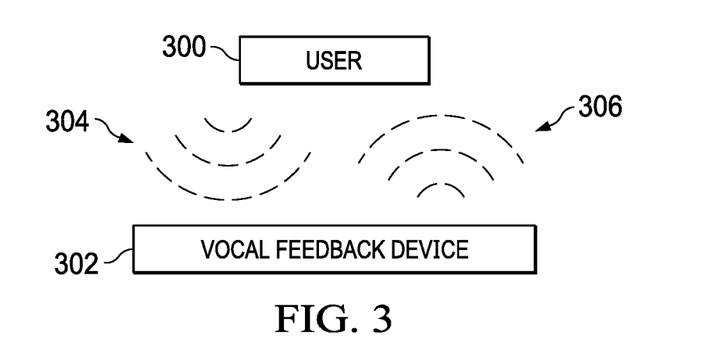
FIG. 3 illustrates a vocal feedback device in use, in accordance with an illustrative embodiment.

FIG. 3 illustrates a vocal feedback device in use, in accordance with an illustrative embodiment. Referring to FIG. 3, vocal feedback device 302 may be one implementation of vocal feedback device 102 in FIG. 1.

User 300 may use vocal feedback device 302 to train the voice of user 300. User 300 utters sound waves 304 which are received by vocal feedback device 302. Sound waves 304 represent the vocal utterances of user 300. Vocal feedback device transmits sound waves 306 heard by user 300. Sound waves 306 represent the sound emitted by vocal feedback device 302. Sound waves 306 are the vocal utterances of user 300 after being delayed and having the fundamental frequency of the utterance detected and accentuated and then transmitted back to user 300 for user 300 to hear with the user's auditory organs. Sound waves 306 represent the user's own voice delayed by vocal feedback device 302 and heard by the user.

Vocal feedback device 302 may create the effect of a resonant room where the output of vocal feedback device 302 heard by the user lacks distracting irrelevant aspects of speech that would cause other people to be aware of the output. For example, the output of vocal feedback device 302 may lack phonemes. Phonemes are any of the perceptually distinct units of sound in a specified language that distinguish one word from another. Phonemes primarily consist of harmonics. The output of vocal feedback device 302 may lack those harmonics, so users and others nearby don't perceive the sound as speech and don't focus on the output.

In an exemplary implementation, the delay implemented by vocal feedback device 302 is long enough to be perceptible by user 300, but not overly distracting to the user. An example of such a delay is about 100 milliseconds for many applications. However, any delay range could be used depending on the application, from several seconds when a user wants to listen to entire phrases played back, down to the minimum processing time of the electronics, for example, no delay from delay circuit 206. In an exemplary implementation, the delay implemented by vocal feedback device 302 is imperceptible to both the user and nearby others.

In addition, vocal feedback device 302 may amplify the vocal utterances of user 300. The amplification factor may result in sounds loud enough to be perceived by the wearer and low enough to not be noticed by nearby others. For example, positioning vocal feedback device 302 at approximately 3 feet from the user, vocal feedback device 302 may amplify the output resulting in positive overall gain perceived by the user while at the same time, the output may not be perceived by others. The sound fidelity may be irrelevant in some applications. Additionally, an exemplary implementation of vocal feedback device 302 contemplates actively using low overall gain over the delay period to reduce self-resonance. For example, a gain of 3 dB over ambient noise. A low gain is considered a gain which prevents a noticeable difference of self-resonance from the perspective of the user. Optionally, feedback cancellation may also be added to further reduce self-resonance.

An exemplary implementation of vocal feedback device 302 includes a discreet vocal feedback device. The term "discreet" is intended to mean a speaker or output transducer of an exemplary vocal feedback device that is not or avoids the use of a headset, earbuds, etc. or any other output transducer that physically contacts the user's ears.

An exemplary implementation of vocal feedback device 302 includes a compact vocal feedback device. The term "compact" is intended to mean vocal feedback device 302 is a small box, perhaps small enough to fit into a shirt pocket and carriable by the user where a directional speaker and a directional microphone directly face the user's ears and mouth, respectively. The term "compact" is also intended to include a device that is not worn but instead is nearby to people (for example, a set top or desk top in a room or vehicle) that provides audio feedback for the same family of purposes. A compact vocal feedback device 302 may be free-standing or attached to a fixture such as ceilings, cubicles, and desks at a distance from the user as much as, for example, ten feet. A compact vocal feedback device may have dimensions less than two inches by two inches by one inch. In this case, vocal feedback device 302 may be electronically independent or connected to a common or networked controller.

An exemplary implementation of vocal feedback device 302 includes a minute vocal feedback device. The term "minute" is intended to mean vocal feedback device 302 includes a microphone or other input transducer and a speaker or other output transducer mounted to a thin and possibly flexible panel, for example 1 mm thick, shaped to be embedded within clothing, for example a shoulder, collar, sleeve, or undergarment or embedded within jewelry such as brooches, earrings, tie-clips, eyeglasses, and any other similarly sized object.

A further exemplary implementation of vocal feedback device 302 is a laptop computer or tablet computer, using its microphone as input transducer and speakers as output transducers where software implements the delay.

Figure 4:
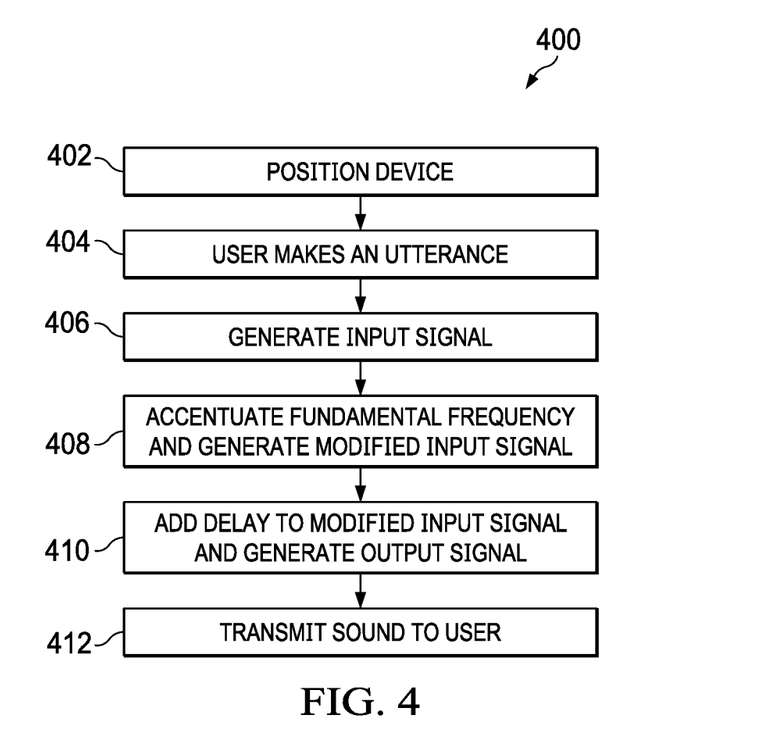
FIG. 4 illustrates a process for using and operating a vocal feedback device, in accordance with an illustrative embodiment.

FIG. 4 illustrates a process for using and operating an exemplary implementation of a vocal feedback device, in accordance with an illustrative embodiment. Process 400 may be implemented using a vocal feedback device such as vocal feedback device 102 in FIG. 1 or vocal feedback device 302 in FIG. 3.

In operation 402, vocal feedback device 102 is positioned. Positioning the vocal feedback device includes pointing microphone 104 and speaker 108 directly at the user at a distance from the user as much as, for example, ten feet. A nondirectional microphone and nondirectional speaker may be positioned within, for example, 1 foot of the user's mouth and ears and still suffice. In operation 404, the user makes an utterance. The user's utterance is received by microphone 104. In operation 406, microphone 104 generates input signal 114. Input signal 114 is electrical signals produced by microphone 104 from the sound waves uttered by the user. In operation 408, FFA subsystem 120 accentuates the fundamental frequency of input signal 114 and generates modified input signal 122. In operation 410, delay circuit 106 adds delay to modified input signal 122 and generates output signal 116. In operation 412, speaker 108 receives output signal 116 and transmits sound directed back to the user.

The vocal feedback device as described in this disclosure creates a direct acoustic path from the mouth to the ear that assists a person to have greater awareness of various aspects of their voice. The vocal feedback device as described in this disclosure receives the sound waves of the user's utterance, modifies the input signal of the microphone to accentuate and amplify the fundamental frequency of the user's utterance, creates an output signal of the modified input signal, adds delay to the output signal, and transmits the delayed output signal as sound waves directly back to the user.

Figure 5:
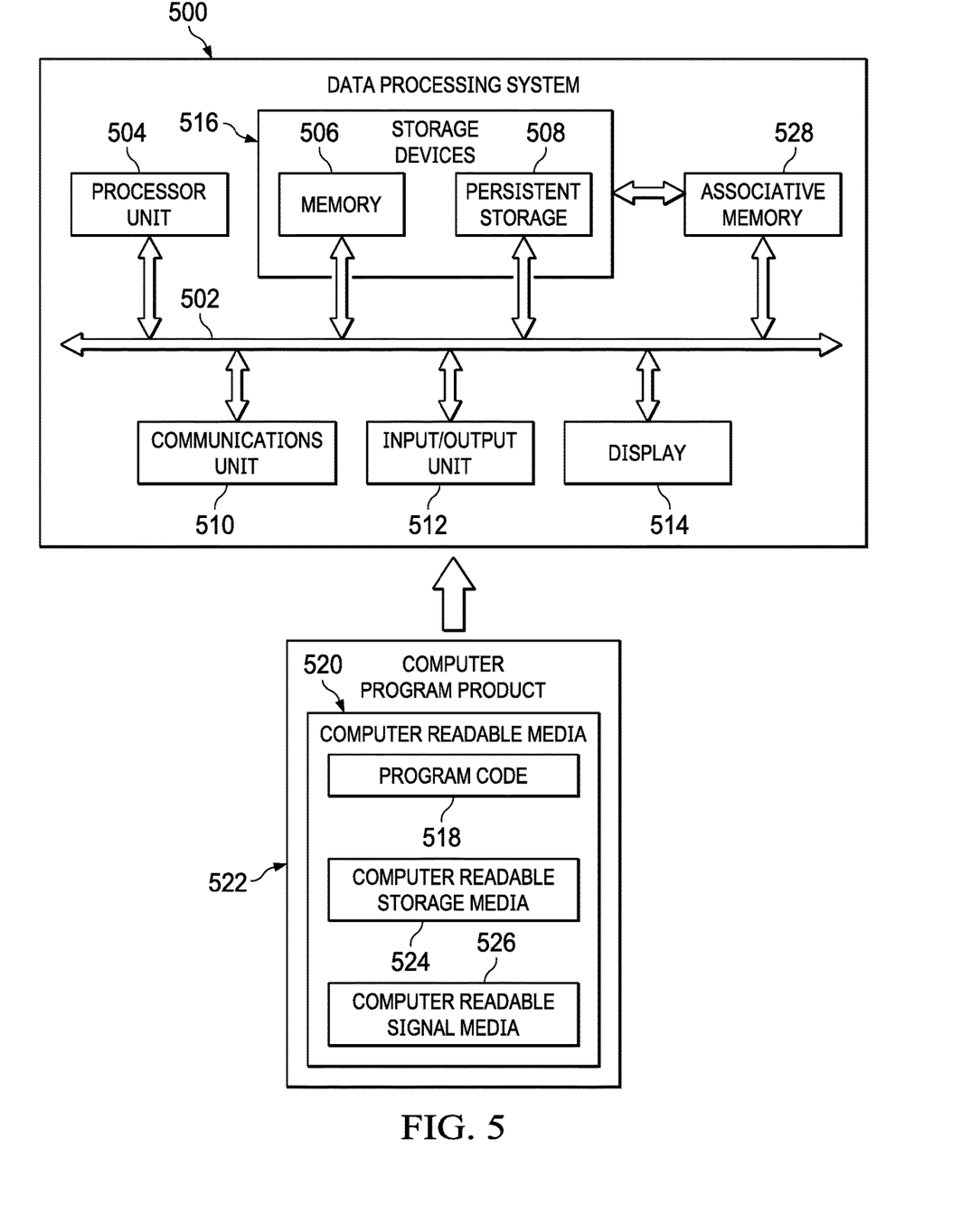
FIG. 5 illustrates a data processing system, in accordance with an illustrative embodiment.

Turning now to FIG. 5, an illustration of a data processing system is depicted in accordance with an illustrative embodiment. Data processing system 500 in FIG. 5 is an example of a data processing system that may be used to implement the illustrative embodiments, such as vocal feedback device 102 of FIG. 1, vocal feedback device 302 of FIG. 3, or any other module or system or process disclosed herein. In this illustrative example, data processing system 500 includes communications fabric 502, which provides communications between processor unit 504, memory 506, persistent storage 508, communications unit 510, input/output (I/O) unit 512, and display 514.

Processor unit 504 serves to execute instructions for software that may be loaded into memory 306. This software may be an associative memory, content addressable memory, or software for implementing the processes described elsewhere herein. Processor unit 504 may be a number of processors, a multi-processor core, or some other type of processor, depending on the particular implementation. A number, as used herein with reference to an item, means one or more items. Further, processor unit 504 may be implemented using a number of heterogeneous processor systems in which a main processor is present with secondary processors on a single chip. As another illustrative example, processor unit 504 may be a symmetric multi-processor system containing multiple processors of the same type.

Memory 506 and persistent storage 508 are examples of storage devices 516. A storage device is any piece of hardware that is capable of storing information, such as, for example, without limitation, data, program code in functional form, and/or other suitable information either on a temporary basis and/or a permanent basis. Storage devices 516 may also be referred to as computer readable storage devices in these examples. Memory 506, in these examples, may be, for example, a random access memory or any other suitable volatile or non-volatile storage device. Persistent storage 508 may take various forms, depending on the particular implementation.

For example, persistent storage 508 may contain one or more components or devices. For example, persistent storage 508 may be a hard drive, a flash memory, a rewritable optical disk, a rewritable magnetic tape, or some combination of the above. The media used by persistent storage 508 also may be removable. For example, a removable hard drive may be used for persistent storage 508.

Communications unit 510, in these examples, provides for communications with other data processing systems or devices. In these examples, communications unit 510 is a network interface card. Communications unit 510 may provide communications through the use of either or both physical and wireless communications links.

Input/output (I/O) unit 512 allows for input and output of data with other devices that may be connected to data processing system 500. For example, input/output (I/O) unit 512 may provide a connection for user input through a keyboard, a mouse, and/or some other suitable input device. Further, input/output (I/O) unit 512 may send output to a printer. Display 514 provides a mechanism to display information to a user.

Instructions for the operating system, applications, and/or programs may be located in storage devices 516, which are in communication with processor unit 504 through communications fabric 502. In these illustrative examples, the instructions are in a functional form on persistent storage 508. These instructions may be loaded into memory 506 for execution by processor unit 504. The processes of the different embodiments may be performed by processor unit 504 using computer implemented instructions, which may be located in a memory, such as memory 506.

These instructions are referred to as program code, computer usable program code, or computer readable program code that may be read and executed by a processor in processor unit 504. The program code in the different embodiments may be embodied on different physical or computer readable storage media, such as memory 506 or persistent storage 508.

Program code 518 is located in a functional form on computer readable media 520 that is selectively removable and may be loaded onto or transferred to data processing system 500 for execution by processor unit 504. Program code 518 and computer readable media 520 form computer program product 522 in these examples. In one example, computer readable media 520 may be computer readable storage media 524 or computer readable signal media 526. Computer readable storage media 524 may include, for example, an optical or magnetic disk that is inserted or placed into a drive or other device that is part of persistent storage 508 for transfer onto a storage device, such as a hard drive, that is part of persistent storage 508. Computer readable storage media 524 also may take the form of a persistent storage, such as a hard drive, a thumb drive, or a flash memory, that is connected to data processing system 500. In some instances, computer readable storage media 524 may not be removable from data processing system 500.

Alternatively, program code 518 may be transferred to data processing system 500 using computer readable signal media 526. Computer readable signal media 526 may be, for example, a propagated data signal containing program code 518. For example, computer readable signal media 526 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 518 may be downloaded over a network to persistent storage 508 from another device or data processing system through computer readable signal media 526 for use within data processing system 500. For instance, program code stored in a computer readable storage medium in a server data processing system may be downloaded over a network from the server to data processing system 500. The data processing system providing program code 518 may be a server computer, a client computer, or some other device capable of storing and transmitting program code 518.

The different components illustrated for data processing system 500 are not meant to provide architectural limitations to the manner in which different embodiments may be implemented. The different illustrative embodiments may be implemented in a data processing system including components in addition to or in place of those illustrated for data processing system 500. Other components shown in FIG. 5 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 504 may take the form of a hardware unit that has circuits that are manufactured or configured for a particular use. This type of hardware may perform operations without needing program code to be loaded into a memory from a storage device to be configured to perform the operations.

For example, when processor unit 504 takes the form of a hardware unit, processor unit 504 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, programmable array logic, a field programmable logic array, a field programmable gate array, and other suitable hardware devices. With this type of implementation, program code 518 may be omitted because the processes for the different embodiments are implemented in a hardware unit.

In still another illustrative example, processor unit 504 may be implemented using a combination of processors found in computers and hardware units. Processor unit 504 may have a number of hardware units and a number of processors that are configured to run program code 518. With this depicted example, some of the processes may be implemented in the number of hardware units, while other processes may be implemented in the number of processors.

As another example, a storage device in data processing system 500 is any hardware apparatus that may store data. Memory 506, persistent storage 508, and computer readable media 520 are examples of storage devices in a tangible form.

In another example, a bus system may be used to implement communications fabric 502 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 506, or a cache, such as found in an interface and memory controller hub that may be present in communications fabric 502.

Data processing system 500 may also include associative memory 528. Associative memory 528 may be in communication with communications fabric 502. Associative memory 528 may also be in communication with, or in some illustrative embodiments, be considered part of storage devices 516. While one associative memory 528 is shown, additional associative memories may be present.

As used herein, the term "associative memory" refers to a plurality of data and a plurality of associations among the plurality of data. The plurality of data and the plurality of associations may be stored in a non-transitory computer readable storage medium. The plurality of data may be collected into associated groups. The associative memory may be configured to be queried based on at least indirect relationships among the plurality of data in addition to direct correlations among the plurality of data. Thus, an associative memory may be configured to be queried based solely on direct relationships, based solely on at least indirect relationships, as well as based on combinations of direct and at least indirect relationships. An associative memory may be a content addressable memory.

Thus, an associative memory may be characterized as a plurality of data and a plurality of associations among the plurality of data. The plurality of data may be collected into associated groups. Further, the associative memory may be configured to be queried based on at least one relationship, selected from a group that includes direct and at least indirect relationships, or from among the plurality of data in addition to direct correlations among the plurality of data. An associative memory may also take the form of software. Thus, an associative memory also may be considered a process by which information is collected into associated groups in the interest of gaining new insight based on relationships rather than direct correlation. An associative memory may also take the form of hardware, such as specialized processors or a field programmable gate array.

As used herein, the term "entity" refers to an object that has a distinct, separate existence, though such existence need not be a material existence. Thus, abstractions and legal constructs may be regarded as entities. As used herein, an entity need not be animate. Associative memories work with entities.

The different illustrative embodiments can take the form of an entirely hardware embodiment, an entirely software embodiment, or an embodiment containing both hardware and software elements. Some embodiments are implemented in software, which includes but is not limited to forms such as, for example, firmware, resident software, and microcode.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible apparatus that can contain, store, communicate, propagate, or transport the program for use by or in connection with the instruction execution system, apparatus, or device.

The computer usable or computer readable medium can be, for example, without limitation an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or computer usable program code such that when the computer readable or computer usable program code is executed on a computer, the execution of this computer readable or computer usable program code causes the computer to transmit another computer readable or computer usable program code over a communications link. This communications link may use a medium that is, for example without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems or remote printers or storage devices through intervening private or public networks. Non-limiting examples of modems and network adapters are just a few of the currently available types of communications adapters.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A vocal feedback device to train a user's voice for improved tonal qualities of speech, comprising:
    a microphone coupled to a delay circuit;
    a fundamental frequency accentuator coupled to a speaker;
    the delay circuit coupled to the fundamental frequency accentuator, where the delay circuit is configured to impose a time delay before transmitting an electrical signal received from the microphone, and where the fundamental frequency accentuator is configured to modify the electric signal before transmitting a modified electrical signal; and
    where the speaker is configured to convert the modified electrical signal to an audio signal to be heard by the user.

2. The vocal feedback device of claim 1, wherein the microphone generates the electrical signal from an utterance of the user's voice and transmits the electrical signal to the delay circuit.

3. The vocal feedback device of claim 1, wherein the microphone is directed at the user and the microphone generates the electrical signal from sound waves of the user's utterance and transmits the electrical signal to the delay circuit.

4. The vocal feedback device of claim 1, wherein the microphone generates the electrical signal from an utterance of the user's voice and the fundamental frequency accentuator attenuates distracting harmonics from a frequency spectrum of the electrical signal.

5. The vocal feedback device of claim 1, wherein the audio signal is a replication of an utterance of the user's voice where the fundamental frequency of the utterance of the user's voice is accentuated.

6. The vocal feedback device of claim 1, further comprising interface electronics configured to alter the time delay.

7. The vocal feedback device of claim 1, wherein the vocal feedback device is discreet.

8. The vocal feedback device of claim 1, wherein the vocal feedback device is compact and carriable by the user.

9. The vocal feedback device of claim 1, wherein the vocal feedback device is minute and embedded in a clothing of the user or a jewelry of the user.

10. A vocal feedback device to assist the speech of a user, comprising:
    a directional microphone pointed at the user and in receipt of input sound waves generated from the speech of the user;
    an electrical signal produced from the input sound waves and generated by the microphone;
    a delay circuit coupled to the microphone;
    a fundamental frequency accentuator coupled to the delay circuit;

a modified electrical signal generated by the fundamental frequency accentuator where a fundamental frequency of the input sound waves is accentuated in the modified electrical signal;

a directional speaker coupled to the fundamental frequency accentuator and pointed at the user; and a time delay introduced to the electrical signal before the modified electrical signal is converted to output sound waves by the speaker.

11. The vocal feedback device of claim 10, wherein the fundamental frequency accentuator attenuates distracting harmonics from a frequency spectrum of the electrical signal.

12. The vocal feedback device of claim 10, wherein the output sound waves are a replication of an utterance of the user's voice where the fundamental frequency of the utterance of the user's voice is accentuated.

13. The vocal feedback device of claim 10, further comprising interface electronics configured to alter the time delay.

14. A method for improving a vocalization of a user, comprising:

positioning a vocal feedback device comprising a microphone coupled to a delay circuit and a fundamental frequency accentuator coupled to the delay circuit and to a speaker;

generating an electrical signal with the microphone from the vocalization;

imposing a delay with the delay circuit on the electrical signal;

generating a modified electrical signal with the fundamental frequency accentuator from the electrical signal; and transmitting sound waves with the speaker generated from the modified electrical signal.

15. The method of claim 14, wherein positioning the vocal feedback device further comprises pointing the microphone of the vocal feedback device directly at the user.

16. The method of claim 14, wherein generating a modified electrical signal further comprises accentuating a fundamental frequency of the electrical signal.

17. The method of claim 14, wherein generating a modified electrical signal further comprises attenuating distracting harmonics from a frequency spectrum of the electrical signal.

18. The method of claim 14, wherein transmitting sound waves further comprises pointing the speaker of the vocal feedback device directly at the user.

19. The method of claim 14, wherein the vocal feedback device is a discreet vocal feedback device and positioning the vocal feedback device further comprises positioning the vocal feedback device such that the speaker of the vocal feedback device does not physically contact an ear of the user.

20. The method of claim 14, wherein the vocal feedback device is a minute vocal feedback device and positioning the vocal feedback device further comprises embedding the vocal feedback device in a clothing of the user or a jewelry of the user.

* * * * *